US011559526B2

(12) United States Patent
Kodama et al.

(10) Patent No.: US 11,559,526 B2
(45) Date of Patent: Jan. 24, 2023

(54) DRUG EFFECTIVE FOR LYMPHOGENOUS DRUG ADMINISTRATING METHOD

(71) Applicants: TOHOKU UNIVERSITY, Sendai (JP); KABUSHIKI KAISHA YAKULT HONSHA, Minato-ku (JP)

(72) Inventors: Tetsuya Kodama, Sendai (JP); Shiro Mori, Sendai (JP); Go Nohara, Minato-ku (JP)

(73) Assignees: TOHOKU UNIVERSITY, Sendai (JP); KABUSHIKI KAISHA YAKULT HONSHA, Minato-ku (JP)

( * ) Notice: Subject to any disclaimer, the term of this patent is extended or adjusted under 35 U.S.C. 154(b) by 43 days.

(21) Appl. No.: 16/339,545

(22) PCT Filed: Aug. 31, 2017

(86) PCT No.: PCT/JP2017/031483
§ 371 (c)(1),
(2) Date: Apr. 4, 2019

(87) PCT Pub. No.: WO2018/066278
PCT Pub. Date: Apr. 12, 2018

(65) Prior Publication Data
US 2020/0038400 A1 Feb. 6, 2020

(30) Foreign Application Priority Data
Oct. 5, 2016 (JP) .............................. JP2016-197614

(51) Int. Cl.
| A61K 31/513 | (2006.01) |
| A61P 35/00 | (2006.01) |
| A61K 31/4745 | (2006.01) |
| A61K 45/00 | (2006.01) |
| A61K 31/337 | (2006.01) |

(52) U.S. Cl.
CPC ........ *A61K 31/513* (2013.01); *A61K 31/4745* (2013.01); *A61K 45/00* (2013.01); *A61P 35/00* (2018.01); *A61K 31/337* (2013.01)

(58) Field of Classification Search
CPC .............. A61K 31/337; A61K 31/4745; A61K 31/513; A61K 45/00; A61P 35/00
See application file for complete search history.

(56) References Cited

U.S. PATENT DOCUMENTS

| 4,631,342 A * | 12/1986 | Umemoto ........... C07D 239/553 544/313 |
| 7,037,906 B1 * | 5/2006 | Lee ..................... A61K 31/337 514/130 |
| 9,655,876 B2 * | 5/2017 | Sonoke .................. A61K 47/14 |
| 2006/0188566 A1 * | 8/2006 | Liversidge ........... A61K 31/337 424/464 |
| 2010/0203163 A1 * | 8/2010 | Allen ..................... A61K 47/24 424/649 |
| 2011/0189265 A1 | 8/2011 | Campisi et al. |
| 2020/0206352 A1 * | 7/2020 | Kodama ............ A61K 31/7088 |

FOREIGN PATENT DOCUMENTS

| CA | 2 972 610 A1 | 7/2016 |
| CN | 101045163 B | 3/2011 |
| JP | 2011-518217 A | 6/2011 |
| WO | WO 03/075917 A1 | 9/2003 |
| WO | WO-2009021840 A1 * | 2/2009 ........... A61K 31/337 |
| WO | WO 2009/130564 A1 | 10/2009 |

OTHER PUBLICATIONS

Osaki et al., "Intranodal injection of anticancer drugs into fixed cervical metastatic lymph nodes", 1997, Oral Diseases, 3(4), pp. 247-253. (Year: 1997).*
Yang et al., "A novel mixed micelle gel with thermo-sensitive property for the local delivery of docetaxel", 2009, Journal of Controlled Release, 135 (2), pp. 175-182. (Year: 2009).*
Gao et al., "A thermo-sensitive PLGA-PEG-PLGA hydrogel for sustained release of docetaxel", 2011, Journal of Drug Targeting, 19(7), pp. 516-527. (Year: 2011).*
Nicolas Huang, "Rheological Characterization of Pharmaceutical and Cosmetic Formulations for Cutaneous Applications", 2019, Current Pharmaceutical Design, 25(21), pp. 2349-2363. (Year: 2019).*
Kestin et al., "Tables of the Dynamic and Kinematic Viscosity of Aqueous NaCl Solutions in the Temperature Range 20-150 °C and the Pressure Range 0.1-35 MPa", 1981, J. Phys. Chem. Ref. Data, vol. 10, No. 1, pp. 71-87. (Year: 1981).*
National Center for Biotechnology Information. "PubChem Compound Summary for CID 60838, Irinotecan" PubChem, https://pubchem.ncbi.nlm.nih.gov/compound/Irinotecan. Accessed Dec. 1, 2021. created Jun. 24, 2005. (Year: 2005).*
Nair et al., "Asimple practice guide for dose conversion between animals and human", 2016, J. Basic Clin. Pharma., 7(2), pp. 27-31. (Year: 2016).*
Viscosity website: https://resources.saylor.org/wwwresources/archived/site/wp-content/uploads/2011/04/Viscosity.pdf. Retrieved on Dec. 1, 2021. (Year: 2021).*
International Search Report dated Oct. 17, 2017 in PCT/JP2017/031486, 4 pages (with English translation).
J. Carr, et al., "Lymphatic Metastasis; Lymphangiochemotherapy of Mammary Cancer: Ascitic Form of rat Mammary Adenocarcinoma 13762", Clinical and Experimental Metastasis, vol. 1, No. 1, 1983, pp. 29-38.
"Interview Form of Hikari Glucose Injection 5%, 10%, 20%, 30% and 50%" Hikari Pharmaceutical Co., LTD., vol. 5, 2015, pp. 1-26 (with partial English translation).

(Continued)

*Primary Examiner* — My-Chau T. Tran
(74) *Attorney, Agent, or Firm* — Oblon, McClelland, Maier & Neustadt, L.L.P.

(57) ABSTRACT

Provided is a pharmaceutical composition suitable for administration of anticancer drugs into lymph nodes by means of lymphatic drug delivery systems. A pharmaceutical composition for therapeutic or prophylactic treatment of cancer to be administered into lymph nodes, comprising at least one anticancer drug selected from the group consisting of antimetabolites and anticancer plant alkaloids as an active ingredient.

5 Claims, 3 Drawing Sheets

(56) References Cited

OTHER PUBLICATIONS

Tetsuya Kodama, et al., "New Concept for the Prevention and Treatment of Metastatic Lymph Nodes Using Chemotherapy Administered Via the Lymphatic Network" Scientific Reports, URL: http://www.tohoku.ac.jp/japanese/2016/09/press20160831-02.html, Sep. 2, 2016. 6 pages (with English translation).

Asuda Tada, et al. "P-3271; Research on Development of Drug Delivery Method Using Lymphatic Network for Metastatic Lymph Nodes" The 75th Annual Meeting of the Japanese Cancer Association Proceedings, URL: https://www.congre.co.jp/jca2016/, Sep. 23, 2016, 2 pages (with English translation).

Office Action dated Feb. 11, 2020 in corresponding Indian Patent Applicatio No. 2019013615 (with English Translation), 6 pages.

Extended European Search Report dated May 15, 2020 in European Patent Application No. 17858117.9, 9 pages.

Shigeki Kato, et al., "A Novel Treatment Method for Lymph Node Metastasis Using a Lymphatic Drug Delivery System with Nano/Microbubbles and Ultrasound", Journal of Cancer, 2015, 6(12), pp. 1282-1294.

V.R.N. Telis, et al., "Viscosity of Aqueous Carbohydrate Solutions at Different Temperatures and Concentrations", International Journal of Food Properties, vol. 10, No. 1, 2007, pp. 185-195.

Combined Russian Office Action and Search Report dated Dec. 14, 2020 for Russian Patent Application No. 2019109965 (with English translation), 24 pages.

Konorev, M.P., et al., "Klinicheskaya farmakologiya (Clinical Pharmacology): a textbook for 6th year students of the medical department", (edited by M.R. Konorev).—Vitebsk: VGMU, 2012, p. 16.

M.D.Mashkovskiy. Lekarstvennye sredstva (Medicinal Agents), 14th edition, vol. 1, Moscow, 2001, p. 11 with cover page (with English translation).

Belikov, V.G., "Farmatsevticheskaya khimiya (Pharmaceutical Chemistry)", Chapter 2.6 "Relationship between the chemical structure, properties of substances, and their effects on the organism".—M.: MEDpress-inform, 2007, pp. 27-29 with cover page (with English translation).

Kharkevich. D.A., Farmakologiya (Pharmacology), M., Meditsina, 1987, pp. 47-48.

Combined Chinese Office Action and Search Report dated Nov. 3, 2020 in Patent Application No. 20178061797.8, dated Nov. 27, 2020 (with English machine translation and English translation of Category of Cited Documents), 20 pages.

Niu Shunhai, "Clinical observation of celecoxib combined with irinotecan in the treatment of adverse reactions of colorectal cancer chemotherapy," Chinese Journal of Clinical Rational Drug Use, vol. 3, No. 17, Sep. 2010, p. 47 (with English Abstract).

Wang Fuxiang, et al., "Observation of the effect of docetaxel combined with Kangai in the treatment of advanced lung cancer," Chinese Community Doctors, vol. 14, No. 5, 2012, p. 102 (with English Abstract).

Zheng Na, "Clinical observation and nursing of low-dose 5-FU continuous intravenos infusion in the treatment of late recurrent tumor," Guide of Chinese Medicine, vol. 9, No. 33, Nov. 2011, pp. 193-194 (with English Abstract).

Office Action dated Apr. 13, 2021 for Taiwanese Patent Application No. 106129854(with machine translation—13 pages).

Instructions for Use of Department of Health Pharmaceuticals No. 048587 Drug License, Mar. 24, 2014, Components and contents (with machine translation of relevant portions—4 pages.

Office Action dated Apr. 26, 2021 for Russian Patent Application No. 2019109965(w/English translation) 10 pages.

Guidelines for experimental (preclinical) research of new pharmacological substances. Edited by R.U. Khabriev, 2nd edition, "Medicine", 2005, pp. 1-832, p. 49) 1 page.

Tetsuya Kodama, et al., "New Concept for the Prevention and Treatment of Metastatic Lymph Nodes Using Chemotherapy Administered Via the Lymphatic Network" Scientific Reports, Article No. 32506, vol. 6, Sep. 1, 2016, pp. 1-8.

* cited by examiner

[Figure 1]
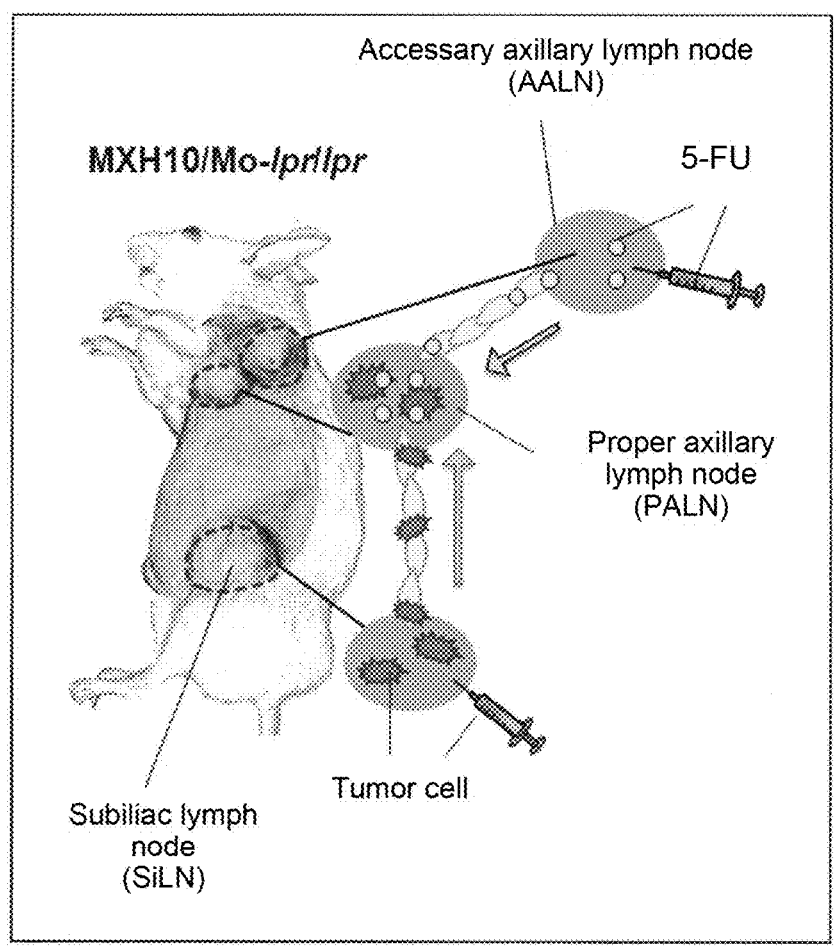

[Figure 2]
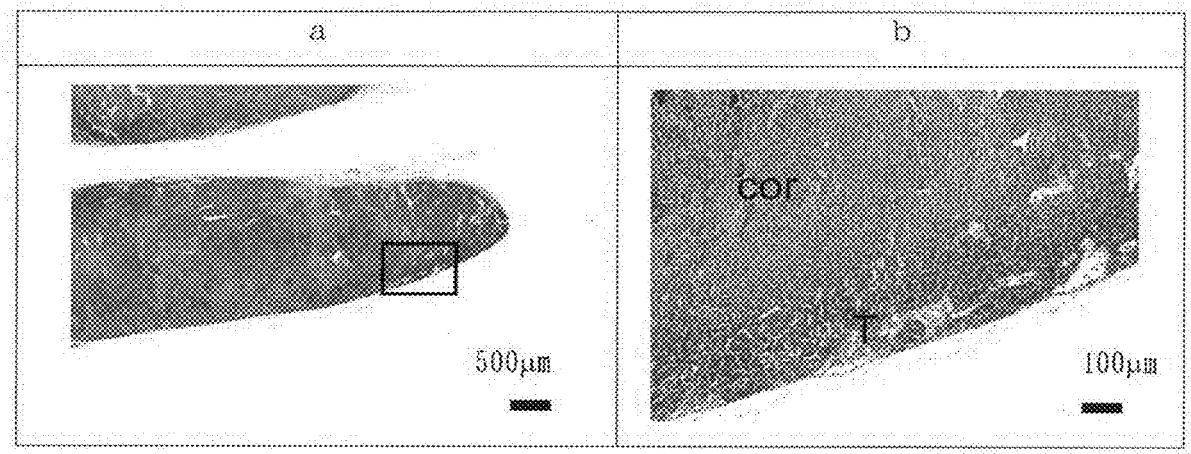
[Figure 3]
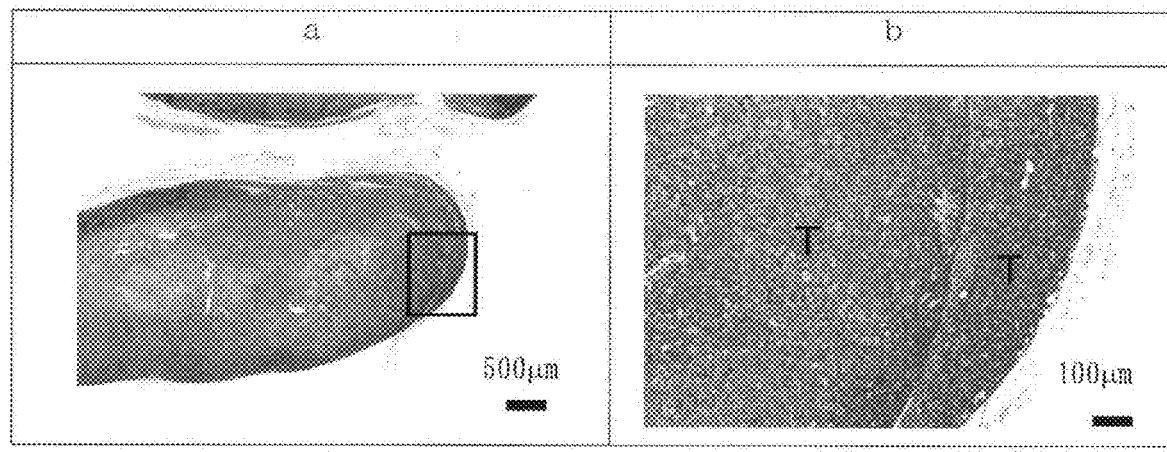

[Figure 4]
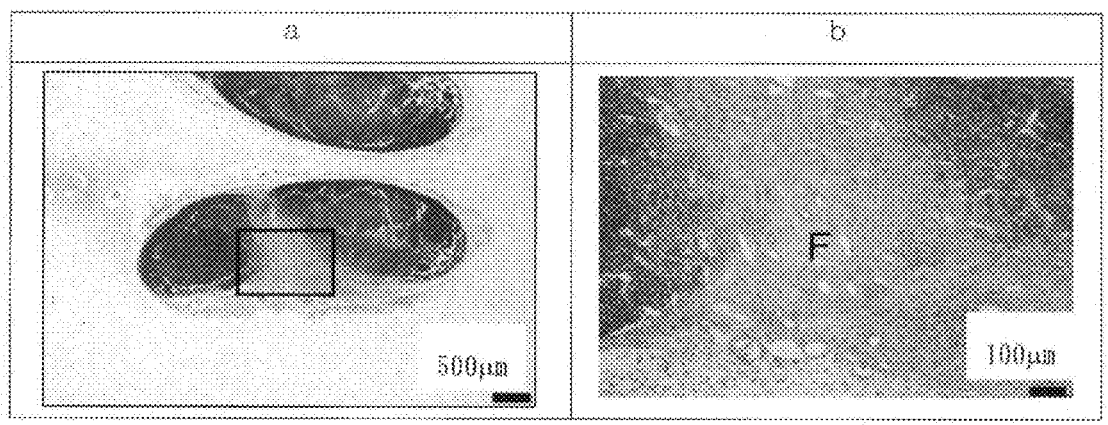

DRUG EFFECTIVE FOR LYMPHOGENOUS DRUG ADMINISTRATING METHOD

TECHNICAL FIELD

The present invention relates to a pharmaceutical composition suitable for lymphatic drug delivery systems.

BACKGROUND ART

Cancer is a disease that afflicts one in two persons in Japan and 90% of cancer patients die of metastasis. In many cancers, including breast cancer and head and neck cancer, cancer cells spread to a regional lymph node through lymphatic vessels. The lymph node in which metastasis first forms is called the sentinel lymph node.

A metastatic lymph node is generally treated by lymphadenectomy, radiotherapy or systemic chemotherapy. Systemic chemotherapy involves the injection of an anticancer drug into a vein. Since an anticancer drug is a small molecule, it is readily resorbed by the capillary blood vessels present in the interstitium around a cancer. As a result, satisfactory therapeutic outcomes are not always obtained by systemic chemotherapy.

Recently, the present inventors successfully established a specific mouse that has lymph nodes equal in size to those in humans. Then, cancer cells were transferred to the lymph node (subiliac lymph node (SiLN)) of the mouse and allowed to spread to the proper axillary lymph node (PALN) to develop a model of lymph node metastasis. In the mouse model, it was found that the administration of doxorubicin through the subiliac lymph node (SiLN) resulted in an anticancer effect in the cancer-containing proper axillary lymph node (PALN) (Non Patent Literature 1).

CITATION LIST

Non-Patent Literature

Non Patent Literature 1: Shigeki Kato, Shiro Mori, Tetsuya Kodama, Journal of Cancer 2015, 6 (12): 1282-1294.

SUMMARY OF THE INVENTION

Technical Problem

One objective of the present invention is to provide a pharmaceutical composition more suitable for the administration of an anticancer drug into a lymph node.

Solution to Problem

The present inventors conducted studies in consideration of the aforementioned circumstances. As a result, they found that an antimetabolite or an anticancer plant alkaloid exerts excellent anticancer activity even at a small dose when administered into a lymph node and that the antimetabolite or anticancer plant alkaloid serves as a useful medical drug for administration into a lymph node. On the basis of the finding, the present invention was accomplished.

More specifically, the present invention relates to the following (1) to (10).
(1) A pharmaceutical composition for therapeutic or prophylactic treatment of cancer to be administered into a lymph node, comprising at least one anticancer drug selected from the group consisting of antimetabolites and anticancer plant alkaloids, as an active ingredient.
(2) The pharmaceutical composition according to (1), wherein the antimetabolite is 5-fluorouracil or a salt thereof.
(3) The pharmaceutical composition according to (1) or (2), wherein the anticancer plant alkaloid is at least one selected from the group consisting of irinotecan, SN-38, docetaxel and salts of these.
(4) The pharmaceutical composition according to any one of (1) to (3), wherein the lymph node as a target for the administration is a lymph node to be therapeutically or prophylactically treated or a lymph node positioned upstream in a lymphatic network to which the lymph node belongs.
(5) The pharmaceutical composition according to any one of (1) to (4), wherein a single dosage amount is 1 ng to 100 mg as the antimetabolite and/or 1 ng to 20 mg as the anticancer plant alkaloid.
(6) The pharmaceutical composition according to any one of (1) to (5), wherein the pharmaceutical composition has a viscosity of 40 mPa·s or less.
(7) The pharmaceutical composition according to any one of (1) to (5), wherein the pharmaceutical composition has a viscosity of 1 to 10 mPa·s.
(8) Use of at least one anticancer drug, selected from the group consisting of antimetabolites and anticancer plant alkaloids, in the manufacture of a pharmaceutical composition for therapeutic or prophylactic treatment of cancer to be administered into a lymph node.
(9) A pharmaceutical composition, comprising at least one anticancer drug selected from the group consisting of antimetabolites and anticancer plant alkaloids, for use in therapeutic or prophylactic treatment of cancer by administration into a lymph node.
(10) A method for therapeutic or prophylactic treatment of cancer, comprising administering a pharmaceutical composition, which contains at least one anticancer drug selected from the group consisting of antimetabolites and anticancer plant alkaloids, into a lymph node of a patient.

Effects of the Invention

The pharmaceutical composition of the present invention for administration into a lymph node exerts an excellent anticancer effect at a low dose. When the composition is administered into a lymph node positioned upstream in the lymphatic network, a lymph node positioned downstream in the lymphatic network also can be a treatment target. Owing to this arrangement, a lymph node in the initial stage of metastasis and a lymph node at a high risk of becoming metastatic can be targets for the therapeutic or prophylactic treatment.

BRIEF DESCRIPTION OF THE DRAWINGS

[FIG. 1] The figure illustrates the proper axillary lymph node in the mouse model of metastasis and the administration of a medical drug to the mouse. First, cancer cells are transplanted to the subiliac lymph node (SiLN) and allowed to spread to the proper axillary lymph node (PALN) through lymphatic vessels. Then, a medical drug is administered to the accessory axillary lymph node (AALN) and allowed to be delivered to the proper axillay lymph node through the lymphatic vessel to treat the metastatic cancer cells.

[FIG. 2] The figure shows photographs (a: 2×, b: 10×) of a pathological image of the proper axillary lymph node on day $9^T$ after the administration of Solution B. Figure b is an enlarged view of the square portion in Figure a; "cor"

indicates the cortex of the lymph node; and "T" indicates a cancer. Residual cancer cells are observed in the lymph node cortical surface layer; however, cancer cells are not observed in the region corresponding to the lymph node marginal sinus.

[FIG. 3] The figure shows photographs (a: 2×, b: 10×) of a pathological image of the proper axillary lymph node on day $9^T$ after administration of Solution C. Figure b is an enlarged view of the square portion in Figure a; and "T" indicates a cancer. Infiltration/growth of a cancer is observed in the lymph node parenchyma and the marginal sinus.

[FIG. 4] The figure shows photographs (a: 2×, b: 10×) of a pathological image of the accessory axillary lymph node on day 9 after administration of Solution C. Figure b is an enlarged view of the square portion in Figure a; and "F" indicates fibrosis. Necrosis and fibrosis are observed in a wide region around the lymph node medulla. Pathological changes are evident from the lymph node cortex to the region outside the lymph node capsule including the basal portion of the efferent lymphatic vessel. Stasis of the efferent lymphatic vessel is suggested.

DESCRIPTION OF EMBODIMENTS

The pharmaceutical composition of the present invention comprises at least one anticancer drug selected from the group consisting of antimetabolites and anticancer plant alkaloids and is to be locally administered into a lymph node.

Examples of the antimetabolite include a fluorinated pyrimidine anticancer drug such as 5-fluorouracil (5-FU), a 5-FU prodrug (for example, tegafur or a salt thereof), capecitabine or a salt thereof, TS-1 (also referred to as S-1; a combination drug having tegafur and a modulator in combination), carmofur and doxifluridine. Other than these, gemcitabine, cytarabine, enocitabine, mercaptopurine, fludarabine, cladribine, methotrexate, pemetrexed, hydroxycarbamide, nelarabine, pentostatin and prodrugs of these are mentioned. A fluorinated pyrimidine anticancer drug, which is present in the form of 5-fluorouracil in vivo, is more preferable, and 5-fluorouracil or a salt thereof is particularly preferable.

Examples of the salt thereof herein include a salt thereof with a pharmaceutically acceptable inorganic acid (for example, hydrochloric acid, sulfuric acid, hydrobromic acid, hydroiodic acid, nitric acid, and phosphoric acid) and a pharmaceutically acceptable organic acid (for example, formic acid, acetic acid, propionic acid, malonic acid, succinic acid, glutaric acid, fumaric acid, maleic acid, lactic acid, malic acid, citric acid, tartaric acid, benzenesulfonic acid, p-toluenesulfonic acid and methanesulfonic acid).

Examples of the anticancer plant alkaloid include vincristine, vinblastine, vindesine, vinorelbine, etoposide, irinotecan or an active metabolite thereof or a salt of these, nogitecan, sobuzoxane, docetaxel, paclitaxel, a paclitaxel injection and eribulin; and irinotecan or a metabolite thereof or a salt of these are preferable. An example of an active metabolite of irinotecan is 7-ethyl-10-hydroxycamptothecin (SN-38).

Examples of the salt of irinotecan include a salt thereof with the above-mentioned pharmaceutically acceptable inorganic acid or organic acid; and a hydrochloride thereof is preferable.

The content of an anticancer drug in the pharmaceutical composition of the present invention per unit dosage form, which varies depending on the type thereof, is 1 ng to 1,000 mg, preferably 10 ng to 100 mg, more preferably 100 ng to 10 mg and even more preferably 1 μg to 1 mg.

Since the pharmaceutical composition of the present invention is administered into a lymph node, the composition preferably has a dosage form that is injectable into a lymph node. Examples of the injectable dosage form include an injectable solution, an injectable suspension, an injectable emulsion, an injectable gel and an injectable solid.

Examples of the injectable solid include a lyophilized preparation and a preparation filled with powder, which are to be mixed with a solvent such as water for injection, saline for injection and a glucose solution for injection so as to be used as an injection into a lymph node at the time of use.

The pharmaceutical composition of the present invention can contain a pharmaceutically acceptable carrier, diluent or excipient, in addition to the above anticancer drug. In this case, the pharmaceutically acceptable carrier, diluent or excipient can be appropriately selected from the group consisting of a water-soluble solvent, a lipid-soluble solvent, a dispersant, a tonicity agent, a preservative, a solubilizer, a stabilizer, and the like.

Examples of the water-soluble solvent herein include distilled water, physiological saline, Ringer's solution and phosphate-buffered saline (PBS). Examples of the lipid-soluble solvent include vegetable oils such as olive oil, castor oil, sesame oil, cotton-seed oil and corn oil. Examples of the dispersant include tween 20 or tween 80, polyethylene glycol, carboxymethyl cellulose and sodium alginate. Examples of the tonicity agent include sodium chloride, glycerol, sorbyl alcohol and glucose. Examples of the solubilizer include sodium salicylate, poloxamer and sodium acetate. Examples of the preservative include methylparaben, propylparaben, benzyl alcohol, chlorobutanol, sodium benzoate and phenol. Examples of the stabilizer include albumin such as human serum albumin and bovine serum albumin.

The pharmaceutical composition can be prepared by using the anticancer drug of the present invention in accordance with a known formulation technique; for example, by dissolving, suspending or emulsifying the anticancer drug of the present invention in a water-soluble solvent or a lipid-soluble solvent together with, e.g., a dispersant, a tonicity agent, a preservative, a solubilizer and a stabilizer as mentioned above.

The pharmaceutical composition of the present invention, in view of the tumor regression effect, preferably has a viscosity of 40 mPa·s or less, more preferably 30 mPa·s or less, more preferably 20 mPa·s or less and even more preferably 10 mPa·s or less; and preferably 0.5 mPa·s or more and more preferably 1 mPa·s or more.

More specifically, the viscosity is preferably 0.5 to 40 mPa·s, more preferably 0.5 to 30 mPa·s, more preferably 0.5 to 20 mPa·s, more preferably 0.5 to 10 mPa·s and even more preferably 1 to 10 mPa·s.

The viscosity can be measured by a vibration viscometer (for example, a tuning-fork vibration viscometer <SV-1A, manufactured by A&D Company Ltd.>) at 20° C., as described later in Examples.

Viscosity can be controlled by the use of various hydrophilic polymers generally used as a thickener in an injection preparation. Examples thereof include a linear polysaccharide such as cellulose, amylose, pectin, gelatin, dextrin and alginate; a cellulose derivative (e.g., methylcellulose (MC), a hydroxyalkylcellulose such as hydroxypropylcellulose (HPC) and hydroxypropylmethylcellulose (HPMC), a carboxyalkylcellulose and carboxymethylcellulose (CMC), and salts of these); glycosaminoglycan (e.g., non-sulfated glycosaminoglycan such as hyaluronic acid and a salt thereof, desulfated heparin, desulfated chondroitin sulfate and desulfated dermatan sulfate); galactomannan (e.g., guar gum, fenugreek gum, tara gam, locust bean gum and carob bean gum); carbomer; polyacrylic acid; polycarbophil; polyvinylpyrrolidone; polyacrylamide; polyvinyl alcohol; a derivative of polyvinyl acetate; and a mixture of these. Other than these, a polyoxyethylene sorbitan fatty acid ester also can be used as a stabilizer, a surfactant, a suspending agent, an emulsifier, a dispersant, a solvent, a solubilizer and a solubilizing agent. In view of the tumor regression effect, a polyoxyethylene sorbitan fatty acid ester is preferably used. As the polyoxyethylene sorbitan fatty acid ester, polyoxyethylene sorbitan monolaurate (polysorbate 20, Tween 20), polyoxyethylene sorbitan monostearate (polysorbate 60, Tween 60), polyoxyethylene sorbitan tristearate (polysorbate 65, Tween 65) and polyoxyethylene sorbitan oleate (polysorbate 80, Tween 80) are preferable, and polyoxyethylene sorbitan oleate is more preferable.

The pharmaceutical composition of the present invention thus prepared is locally administered into a lymph node of a patient. An administration target, i.e., a lymph node, herein may be the parenchyma of a lymph node to be therapeutically or prophylactically treated (target lymph node) or a lymph node positioned upstream in the lymphatic network to which the lymph node belongs. Examples of the lymph node include a sentinel lymph node to which cancer cells migrate from a primary lesion and first form metastasis, a lymph node (secondary lymph node) positioned downstream of the sentinel lymph node, a lymph node positioned upstream of a regional lymph node surrounding the primary lesion, and a lymph node positioned upstream in the lymphatic network to which the regional lymph node belongs.

The target lymph node herein may or may not have cancer present. For example, before a lymph node is dissected, the pharmaceutical composition of the present invention is administered into a lymph node (upstream lymph node) within a dissection region to thereby deliver an anticancer drug to a lymph node (downstream lymph node) outside the dissection region through the lymphatic network, and thereafter, dissection is carried out. In this manner, a prophylactic treatment of the downstream lymph node can be made.

The method for administering the pharmaceutical composition of the present invention into a lymph node is not limited as long as the pharmaceutical composition of the present invention can be injected into the lymph node. The composition may be administered by injection into a lymph node exposed by incision of the patient's skin or administered by injection over a site of the patient's skin under which a target lymph node is presumably present.

As shown later in Examples, 5-fluorouracil, irinotecan and docetaxel each exert an excellent anticancer effect at a small dose by administration into a lymph node, as compared to systemically administered doxorubicin. Since it is known that the cell growth inhibitory activity ($GI_{50}$ value) of doxorubicin in a cancer cell strain is extremely strong compared to 5-fluorouracil and irinotecan and equivalent to docetaxel (see Comparative Example), the anticancer effect obtained by administration of 5-fluorouracil, irinotecan or docetaxel into a lymph node cannot be predicted based on common technical knowledge.

The anticancer effect is exerted by administration into a lymph node positioned upstream of a target lymph node to be prophylactically or therapeutically treated. Thus, the pharmaceutical composition of the present invention can be applied to a lymph node in the initial stage of metastasis and a lymph node at a high risk of becoming metastatic as a target for the therapeutic or prophylactic treatment, and is particularly useful for the prevention of recurrence, etc.

Note that, in the specification, the "treatment" refers to a treatment for a subject with cancer (immediate treatment) and means improving, mitigating or eliminating a disease state thereof or one or more symptoms produced by the disease state. The "prophylactic treatment" refers to a treatment for a subject at a risk of developing cancer and currently having no disease state and symptoms.

The type of cancer that can be treated by administering the pharmaceutical composition of the present invention is not particularly limited as long as it exhibits sensitivity to the anticancer drug of the present invention. Examples thereof include head and neck cancer, stomach cancer, colon cancer, rectal cancer, liver cancer, gallbladder/biliary tract cancer, pancreatic cancer, lung cancer, breast cancer, bladder cancer, prostate cancer, uterine cancer, pharyngeal cancer, esophageal cancer, renal cancer and ovarian cancer. Particularly, the composition is expected to exert a high effect on colon cancer, rectal cancer, breast cancer, esophageal cancer, stomach cancer, head and neck cancer, lung cancer, pancreatic cancer and gallbladder/biliary tract cancer.

The frequency of administration and dosage amount of the pharmaceutical composition of the present invention to a human subject can be appropriately controlled or changed. The administration interval is, for example, once in 1 to 42 days, preferably once in 1 to 28 days and more preferably once in 1 to 21 days.

The single dosage amount of the composition as an antimetabolite is 1 ng to 100 mg, preferably 10 ng to 10 mg and more preferably 100 ng to 1 mg, which is about $1/10^9$ to $1/3$ of the dosage amount conventionally used for systemic administration. The single dosage amount of the composition as an anticancer plant alkaloid is 1 ng to 20 mg, preferably 10 ng to 10 mg and more preferably 100 ng to 1 mg, which is about $1/10^7$ to $2/3$ of the dosage amount conventionally used for systemic administration.

Now, the present invention will be more specifically described by way of Examples; however, the present invention is not limited to these Examples.

EXAMPLES

Example 1. Anticancer Activity of 5-FU Administered Into a Lymph Node

1. Materials
(a) Animal Used

As a mouse model of lymphadenopathy, MXH10/Mo/lpr/lpr (MXH10/Mo/lpr) mice were prepared in accordance with the method previously reported (J Immunol Methods 2013; 389 (1-2): 69-78 doi 10.1016/j.jim.2013.01.004). In the following Examples, in total, 5 male and female model mice aged 15 to 18 weeks were used.
(b) Cancer Cells Mouse fibroblast-derived KM-Luc/GFP cells were prepared in accordance with the method previously reported (PLoS One 2013; 8 (2): e55797 doi 10.1371/journal.pone.0055797). The KM-Luc/GFP cells were obtained by transfecting MRL/MpTn-gld/gld mouse fibroblast-derived cancer cells, MRL/N1 cells, with pEGFPLuc plasmid. The KM-Luc/GFP cells constantly express a luciferase gene and a green fluorescent gene. In the following Examples, the cells were cultured in Dulbecco's modified Eagle's medium (manufactured by Sigma-Aldrich) containing 10% FBS (fetal bovine serum), 1% L-Glutamine-P.S. solution (manufactured by Thermo Fisher Scientific) and 0.5% G418 and put in use.

(c) Test Drug

As 5-FU, 5-FU injection, 250 mg (manufactured by Kyowa Hakko Kirin Co., Ltd.) was used. The concentration thereof was controlled with physiological saline so as to be 0 µg/g, 0.1 µg/g, 1 µg/g and 10 µg/g of mouse body-weight.

2. Method (a) Preparation of the Mouse Model of Proper Axillary Lymph Node Metastasis KM-Luc/GFP (cancer) cells, which were prepared by thawing the cells stored at −80° C. and thereafter subculturing them twice in total, were suspended in PBS (phosphate buffered saline) and the concentration thereof was controlled to be $1.0 \times 10^6$ cells/mL. Thereafter, the cell suspension was mixed with Matrigel (basement membrane matrix, manufactured by Becton, Dickinson and Co.) and diluted to a concentration of $3.3 \times 10^5$ cells/mL, and then, the resultant (60 µL) was inoculated into mouse subiliac lymph node (FIG. 1). The day when the cancer cells were inoculated was specified as day 0.

(b) Evaluation of Cancer Cell Growth In Vivo

Using a biological fluorescence imaging system (IVIS manufactured by Caliper Life Science), the growth rates of cancer cells in the subiliac lymph node and proper axillary lymph node were determined on day 0, day 6 and day 9 after inoculation of the cancer cells. 200 µL of luciferin (manufactured by Promega), the concentration of which was controlled to be 15 mg/mL, was injected into the abdominal cavity of the mouse. Ten minutes later, luciferase activity was determined using the IVIS.

(c) Administration of Medical Drug Through Accessory Axillary Lymph Node

Of the mice on day 6 after cancer cell inoculation, mice having a luciferase activity of $1.0 \times 10^6$ photons/sec or more in the proper axillary lymph node were selected, and 120 µL of 5-FU was administered to the accessory axillary lymph node at a rate of 10 µL/min by use of a syringe pump (KDS100, manufactured by Muromachi) (FIG. 1).

(d) Evaluation of Anticancer Activity

The luciferase activities on day 6 and day 9 were normalized in accordance with the following [Expression 1]. Thereafter, the ratio of the normalized luciferase activity on day 9 to that on day 6 was calculated in accordance with the following [Expression 2]. The ratio of the normalized luciferase activity on day 9 to that on day 6 at each administration concentration of 5-FU, when the ratio of the normalized luciferase activity on day 9 to that on day 6 at administration of 0 µg/g was set to 100, was calculated in accordance with the following [Expression 3].

Normalized luciferase activity on day 6 or day 9=((luciferase activity on day 6 or day 9)/(luciferase activity on day 0))  [Expression 1]

Ratio of normalized luciferase activity on day 9 to that on day 6=((normalized luciferase activity on day 9)/(normalized luciferase activity on day 6))  [Expression 2]

Ratio of normalized luciferase activity on day 9 to that on day 6 at each administration concentration of 5-FU, when the ratio of normalized luciferase activity on day 9 to that on day 6 at administration of 0 µg/g was set to 100,=((ratio of normalized luciferase activity on day 9 to that on day 6 at each administration concentration of 5-FU)/(ratio of normalized luciferase activity on day 9 to that on day 6 at administration of 0 µg/g)×100)  [Expression 3]

3. Results

The results are shown in Table 1.

TABLE 1

| Concentration of 5-FU (µg/g) | Luciferase activity ratio calculated by Expression 3 |
|---|---|
| 0 | 100 |
| 0.1 | 9.27 |
| 1 | 9.12 |
| 10 | 1.49 |

It was confirmed that the luciferase activity ratio was drastically decreased and the cancer was reduced in size by the administration of 5-FU and that a tumor regression effect of 90% or more was obtained even with an extremely small dose (0.1 µg/g). 5-FU was administered through the accessory axillary lymph node present upstream of the lymph nodes, and anticancer activity was confirmed in the proper axillary lymph node present downstream thereof. From the above, it was suggested that administration of a small amount of 5-FU to a lymph node, particularly a lymph node present upstream, is useful for, e.g., cancer treatment, recurrence prevention and metastasis prevention, and is, in particular, highly effective for, e.g., treatment and recurrence prevention in a lymph node present downstream. In addition, since anticancer activity was exhibited even at an extremely small dose, it was suggested that this method is highly safe with reduced adverse effects.

Example 2. Anticancer Activity of Irinotecan Hydrochloride (CPT-11) Administered Into a Lymph Node 1. Material The same animal and cells as in Example 1 were used.

As the test drug, CPT-11, i.e., irinotecan hydrochloride (manufactured by Yakult Honsha Co., Ltd.), was used. Irinotecan hydrochloride was dissolved with physiological saline, and the concentration thereof was controlled to be 0 µg/g, 0.5 µg/g and 5 µg/g of mouse body-weight.

2. Method

The same method as in Example 1 was employed except that the test drug to be administered to the accessory axillary lymph node was changed to CPT-11.

3. Results

The results are shown in Table 2.

TABLE 2

| Concentration of CPT-11 (µg/g) | Luciferase activity ratio calculated, by Expression 3 |
|---|---|
| 0 | 100 |
| 0.5 | 6.06 |
| 5 | 3.03 |

It was confirmed that the luciferase activity ratio was drastically decreased and the cancer was reduced in size by the administration of CPT-11 and that a tumor regression effect of 90% or more was obtained even at an extremely small dose (0.5 µg/g). CPT-11 was administered through the accessory axillary lymph node present upstream of the lymph nodes, and anticancer activity was confirmed in the proper axillary lymph node present downstream thereof. From the above, it was suggested that the administration of a small amount of CPT-11 to the lymph node, particularly a lymph node present upstream, is useful for, e.g., cancer treatment and recurrence prevention, and is, in particular, highly effective for, e.g., treatment and recurrence prevention in a lymph node present downstream. In addition, since anticancer activity was exhibited even at an extremely small dose, it was suggested that this method is highly safe with reduced adverse effects.

Example 3. Anticancer Activity of Docetaxel Administered Into a Lymph Node

1. Materials
(a) Animal Used
The same animal as in Example 1 was used.
(b) Cancer Cells
Mouse breast cancer cell-derived FM3A-Luc cells were prepared in accordance with the method previously reported (J Immunol Methods 2013 Mar 29; 389 (1-2): 69-78. doi: 10.1016/j.jim.2013.01.004.). The FM3A-Luc cells were obtained by gene-introduction of pGL4.51 into FM3A cells by means of electroporation and constantly express a luciferase gene. In the following Examples, the cells were cultured in RPMI-1640 (manufactured by Sigma-Aldrich) containing 10% FBS (fetal bovine serum), 1% of an L-Glutamine-P.S. solution (manufactured by Theimo Fisher Scientific) and 0.5% of G418 and put in use.
(c) Test Drug
As docetaxel, taxotere for intravenous infusion, 80 mg (manufactured by Sanofi K. K.) was used. Taxotere for intravenous infusion 80 mg (2 mL) was dissolved in 13% ethanol (6 mL) to prepare a 10 mg/mL stock solution. Thereafter, the stock solution was dissolved with sterile water in such a way that the concentration per mouse body-weight became 0 μg/g, 1 μg/g and 10 μg/g.
2. Method
(a) Preparation of the Mouse Model of Proper Axillary Lymph Node Metastasis
FM3A-Luc (cancer) cells, which were prepared by thawing the cancer cells stored at −80° C. and thereafter subculturing them twice in total, were suspended with PBS (phosphate buffered saline) and the concentration thereof was controlled to be $1.0 \times 10^6$ cells/mL. Thereafter, the cell suspension was mixed with Matrigel (basement membrane matrix, manufactured by Becton, Dickinson and Co.) and diluted up to a concentration of $3.3 \times 10^5$ cells/mL, and then, the resultant (60 μL) was inoculated into mouse subiliac lymph node (FIG. 1). The day when the cancer cells were inoculated was specified as day 0.
(b) Evaluation of Cancer Cell Growth In Vivo
Using a biological fluorescence imaging system (IVIS manufactured by Caliper Life Science), the growth rates of cancer cells in the subiliac lymph node and proper axillary lymph node were determined on day 0, day 7, day 14, day 17, day 20, day 23, day 26 and day 29 after inoculation of the cancer cells. 200 μL of luciferin (manufactured by Promega), the concentration of which was controlled to be 15 mg/mL, was injected into the abdominal cavity of the mouse. Ten minutes later, luciferase activity was determined using the IVIS.
(c) Administration of Medical Drug Through the Accessory Axillary Lymph Node
To a mouse confirmed to have a luciferase activity of $1.0 \times 10^6$ photons/sec or more in the proper axillary lymph node, docetaxel (120 μL) was administered to the accessory axillary lymph node on the day following confirmation at a rate of 10 μL/min by use of a syringe pump (KDS100, manufactured by Muromachi) (FIG. 1).

(d) Evaluation of Anticancer Activity
The day when docetaxel was administered was defined as day $0^T$. The luciferase activity on day $3^T$ (3 days after administration of docetaxel) and the luciferase activity on day $6^T$ (6 days after administration of docetaxel) were normalized in accordance with the following [Expression 4]. Thereafter, the ratio of the normalized luciferase activity on day $3^T$ or day $6^T$ to that on day $-1^T$ (the day when the luciferase activity in the proper axillary lymph node was confirmed to be $1.0 \times 10^6$ photons/sec or more and the day before docetaxel administration) was calculated in accordance with the following [Expression 5]. The ratio of the normalized luciferase activity on day $3^T$ or day $6^T$ to that on day $-1^T$ at each administration concentration of docetaxel, when the ratio of the normalized luciferase activity on day $3^{T \text{ or day}} 6^T$ to that on day $-1^T$ at administration of 0 μg/g was set to 100, was calculated in accordance with the following [Expression 6].

Normalized luciferase activity on day $3^{T, \text{ day}} 6^T$ or day $-1^T$=((luciferase activity on day $3^T$, day $6^T$ or day $-1^T$)/(luciferase activity on day $0^T$)) [Expression 4]

Ratio of normalized luciferase activity on day $3^T$ or day $6^T$ to that on day $-1^T$=((normalized luciferase activity on day $3^T$ or day $6^T$)/(normalized luciferase activity on day $-1^T$)) [Expression 5]

Ratio of normalized luciferase activity on day $3^T$ or day $6^T$ to that on day $-1^T$ at each administration concentration of docetaxel, when the ratio of normalized luciferase activity on day $3^T$ or day $6^T$ to that on day $-1^T$ at administration of 0 μg/g was set to 100,=((ratio of normalized luciferase activity on day $3^T$ or day $6^T$ to that on day $-1^T$ at each administration concentration of docetaxel)/(ratio of normalized luciferase activity on day $3^T$ or day $6^T$ to that on day $-1^T$ at administration of 0 μg/g)×100) [Expression 6]

3. Results
The results are shown in Table 3.

TABLE 3

| Concentration of docetaxel (μg/g) | Luciferase activity ratio calculated by Expression 6 (day $3^T$) | Luciferase activity ratio calculated by Expression 6 (day $6^T$) |
| --- | --- | --- |
| 0 | 100 | 100 |
| 1 | N.D. | 7.5 |
| 10 | 16.2 | 1.7 |

N.D.: No data

It was confirmed that the luciferase activity ratio was drastically decreased and the cancer was reduced in size by the administration of docetaxel and that a tumor regression effect of 90% or more was obtained even at a small dose (1 μg/g) on day 6 after initiation of a treatment. Docetaxel was administered through the accessory axillary lymph node present upstream of the lymph node and anticancer activity was confirmed at the proper axillary lymph node present downstream thereof. From the above, it was suggested that administration of a small amount of docetaxel to a lymph node, particularly a lymph node present upstream, is useful for, e.g., cancer treatment, recurrence prevention and metastasis prevention, and is, in particular, highly effective for, e.g., treatment and recurrence prevention in a lymph node present downstream. In addition, since anticancer activity was exhibited even at an extremely small dose, it was suggested that this method is highly safe with reduced adverse effects.

Example 4. Anticancer Activity of Docetaxel Having Different Viscosities Administered Into a Lymph Node 1. Material The same animal as in Example 1 was used.

The same cells as in Example 4 were used.

As docetaxel, taxotere for intravenous infusion, 80 mg (manufactured by Sanofi K. K.) was used. Taxotere for intravenous infusion 80 mg (2 mL) was dissolved in 13% ethanol (6 mL) to prepare a 10 mg/mL stock solution. Thereafter, Solution A, Solution B and Solution C were prepared in accordance with the blending ratios shown in Table 4 in such a way that the docetaxel concentration per mouse body-weight became 1 μg/g.

TABLE 4

| Name of solution | Solution A | Solution B | Solution C |
|---|---|---|---|
| Polysorbate 80 (μL) | 205 | 830 | 1455 |
| 13% ethanol (μL) | 615 | 2490 | 4365 |
| Distilled, water (μL) | 5000 | 2500 | 0 |
| 10 mg/mL docetaxel (μL) | 180 | 180 | 180 |
| Total (μL) | 6000 | 6000 | 6000 |

* Polysorbate 80 (NOF CORPORATION)

2. Method (a) Preparation of the mouse model of proper axillary lymph node metastasis, (b) Evaluation of cancer cell growth in vivo and (c) Administration of medical drug through the accessory axillary lymph node were carried out in the same manner as in Example 4.

(d) Evaluation of Anticancer Activity

The day when Solution A, B or C was administered was defined as day $0^T$. The luciferase activity on day $9^T$ relative to that on day $-1^T$ (the day when the luciferase activity in the proper axillary lymph node was confirmed to be $1.0 \times 10^6$ photons/sec or more and the day before the docetaxel administration) was calculated in accordance with the following [Expression 7].

Luciferase activity on day $9^T$ relative to that on day $-1^T$=(luciferase activity on day $9^T$)/(luciferase activity on day $-1^T$)     [Expression 7]

(e) Measurement of Viscosity

The viscosity values of Solution A, Solution B and Solution C were measured using a tuning-fork vibration viscometer (SV-1A: viscosity measurement range: 0.3 to 10,000 mPa·s; SV-1H: viscosity measurement range: 0.3 to 1,000 mPa·s, manufactured by A&D Company Ltd.) in accordance with the viscosity measurement method defined by the Japanese Pharmacopoeia.

(f) Photographing of Pathological Images

On day $9^T$ after Solution B or Solution C was administered, pathological images of the proper axillary lymph node and accessory axillary lymph node were observed using an inverted microscope BX51 (manufactured by Olympus Corporation) in accordance with the bright-field observation method and photographed. The magnification was 2× and 10×.

3. Results (a) Relationship Between Viscosity and Luciferase Activity

The results are shown in Table 5.

TABLE 5

| | Viscosity (mPa · s) | Luciferase activity calculated by Expression 7 |
|---|---|---|
| Solution A | 1.39 | 32.57 |
| Solution B | 4.35 | 31.58 |
| Solution C | 41.3 | 96.12 |

The luciferase activity calculated by Expression 7 was the luciferase activity on day $9^T$ relative to that on day $-1^T$. Therefore, a smaller value indicates better tumor regression on day $9^T$. Since, in the case of Solution A and Solution B, the luciferase activity values were low, it was found that the tumor regression effects of Solution A and Solution B were high. In contrast, little or no tumor regression effect of Solution C was observed. From the above, it is considered that, in order to obtain a tumor regression effect of docetaxel administered into a lymph node, the viscosity thereof is preferably 40 mPa·s or less and particularly preferably 1 to 10 mPa·s.

(b) Photographs of Pathological Images on day $9^T$ in the Case of Administering Solution B and Solution C Pathological images of the proper axillary lymph node on day $9^T$ after administration of Solution B or Solution C are shown in FIG. 2 and FIG. 3, respectively.

In the case of Solution B, residual cancer cells were observed in the lymph node cortical surface layer, but cancer cells were not observed in the region corresponding to the lymph node marginal sinus. In contrast, in the case of Solution C, infiltration/growth of a cancer was observed in the lymph node parenchyma and marginal sinus. From this, a tumor regression effect depending on viscosity was continued also from photographs of pathological images of the proper axillary lymph node.

Note that, when a pathological image of the accessory axillary lymph node, which is the administration site of Solution C, was obtained in a similar manner, necrosis and fibrosis were observed in a wide region around the lymph node medulla. Changes were observed from the lymph node cortex to the region outside the lymph node capsule including the basal portion of the efferent lymphatic vessel. Stasis of the efferent lymphatic vessel was suggested (FIG. 4). The reason for this is considered that Solution C, when administered into an upstream lymph node, i.e., the accessory axillary lymph node, remained in the accessory axillary lymph node without flowing to a downstream lymph node due to its high viscosity. Therefore, it is considered that not only in the case of docetaxel, but also in the case where CPT-11 or SN-38, both of which are anticancer plant alkaloids like docetaxel, or 5-FU, which is an antimetabolite, is administered into a lymph node, the viscosity of the medical drug needs to be 40 mPa·s or less.

Comparative Example. Anticancer Activity of Doxorubicin Administered Into a Lymph Node
1. Material The same animal and cells as in Example 1 were used.

As the test drug, i.e., doxorubicin, doxorubicin hydrochloride (manufactured by Wako) was used. The concentration thereof was controlled with physiological saline so as to be 0 μg/g, 0.1 μg/g, 1 μg/g and 10 μg/g of mouse body-weight.

2. Method

The same method as in Example 1 was employed except that the test drug to be administered to the accessary axillary lymph node was changed to doxorubicin.

3. Results

The results are shown in Table 6. In order to compare the anticancer activity of doxorubicin with those of 5-FU, CPT-11 and docetaxel, the results of Examples 1 to 3 are shown together in Table 6.

TABLE 6

|  | Test drug | Dose of test drug (μg/g) | Luciferase activity ratio* |
|---|---|---|---|
| Example1 | 5-FU | 0 | 100 |
|  |  | 0.1 | 9.27 |
|  |  | 1 | 9.12 |
|  |  | 10 | 1.49 |
| Example2 | CPT-11 | 0 | 100 |
|  |  | 0.5 | 6.06 |
|  |  | 5 | 3.03 |
| Example3 | Docetaxel | 10 | 16.2 |
| Comparative Example | Doxorubicin | 0 | 100 |
|  |  | 0.1 | 40.9 |
|  |  | 1 | 43.2 |
|  |  | 10 | 75.0 |

*The luciferase activity ratios in the case of 5-FU, CPT-11 and doxorubicin were calculated by Expression 3, and the luciferase activity ratio in the case of docetaxel was calculated by Expression 6.

The luciferase activity ratio was decreased by the administration of doxorubicin, but the tumor reduction ratio was low compared to those obtained by 5-FU, CPT-11 and docetaxel. In particular, the tumor reduction ratio obtained by doxorubicin at a dose of 10 μg/g was about 25%, and the best tumor reduction ratio was less than 60% at a dose of 1 μg/g, but the tumor reduction ratios obtained by 5-FU and CPT-11 were 90% or more even at a dose of less than 1 μg/g, and the tumor reduction ratio obtained by docetaxel was 80% or more at a dose of 10 μg/g. From these data, it was suggested that the effects of 5-FU, CPT-11 and docetaxel are high compared to that of doxorubicin.

The cell growth inhibitory activity ($GI_{50}$ value) of doxorubicin against a cancer cell strain is known to be about 10 to 1,000 times as high as those of 5-FU and CPT-11, as shown in Table 7 (an average calculated from $GI_{50}$ values against cell strains described in the NIH DTP database (https://dtp.cancer.gov/dtpstandard/cancerscreeningdata/index.js p)). The activity of docetaxel is known to be almost equal to that of doxorubicin.

TABLE 7

| Name of compound | Average $GI_{50}$ value against cancer cell strain (M) |
|---|---|
| Doxorubicin | $6.63 \times 10^{-8}$ |
| CPT-11 | $1.35 \times 10^{-5}$ |
| 5-FU | $8.99 \times 10^{-7}$ |
| Docetaxel | $2.34 \times 10^{-8}$ |

As shown in Table 7, conventionally, it was considered that the effect of doxorubicin was high compared to those of 5-FU and CPT-11 and almost equal to that of docetaxel. However, in the case of administration into a lymph node, the anticancer activities of 5-FU, CPT-11 and docetaxel were found to be higher than that of doxorubicin, as shown in Table 6. From this data, it was demonstrated that these medical drugs are particularly suitable for administration into a lymph node.

INDUSTRIAL APPLICABILITY

According to the pharmaceutical composition of the present invention, when an anticancer drug is administered into a lymph node before dissection, the anticancer drug can be supplied to a lymph node present downstream of the lymph node into which the drug was administered. As a result, it is possible not only that an anticancer effect is exerted in a target lymph node but also that an anticancer drug can be supplied to other lymph nodes that may potentially have a small cancer spread therein. In this manner, the small cancer is killed to prevent recurrence.

If cancer is present in a lymph node in the region to which surgical dissection cannot be applied, healing by surgery cannot be realized, but the lymph node in the region to which surgical dissection cannot be applied can be treated by supplying an anticancer drug through a lymph node present upstream by using the pharmaceutical composition of the present invention. Further, since the pharmaceutical composition of the present invention contains an anticancer drug in an amount lower than that used in conventional systemic administration, the composition has reduced adverse effects and is highly safe.

The invention claimed is:

1. A pharmaceutical composition, for administration into a lymph node for therapeutic or prophylactic treatment of cancer, comprising at least one anticancer drug comprising docetaxel or a salt thereof,
    wherein the pharmaceutical composition has a viscosity of from 1 to 10 mPa·s, and
    wherein the pharmaceutical composition comprises from 1 ng to 20 mg of docetaxel or a salt thereof.

2. A method of manufacturing a pharmaceutical composition for administration into a lymph node for therapeutic or prophylactic treatment of cancer, the method comprising:
    adding at least one anticancer drug comprising docetaxel or a salt thereof, to a composition,
    wherein the pharmaceutical composition has a viscosity of 1 to 10 mPa·s, and
    wherein the pharmaceutical composition comprises from 1 ng to 20 mg of docetaxel or a salt thereof.

3. A method for therapeutically or prophylactically treating cancer, the method comprising:
    administering a pharmaceutical composition comprising at least one anticancer drug comprising docetaxel or a salt thereof, into a lymph node of a patient,
    wherein the pharmaceutical composition has a viscosity of 1 to 10 mPas, and
    wherein the pharmaceutical composition comprises from 1 ng to 20 mg of docetaxel or a salt thereof.

4. The method of claim 3, wherein the lymph node is a lymph node suitable for therapeutic or prophylactic treatment or a lymph node positioned upstream in a lymphatic network to which the lymph node belongs.

5. The pharmaceutical composition of claim 1, wherein the pharmaceutical composition comprises from 1 ng to 1 mg of docetaxel or a salt thereof.

* * * * *